United States Patent
Shaaban et al.

(10) Patent No.: US 11,964,947 B1
(45) Date of Patent: Apr. 23, 2024

(54) MULTI-TARGET DRUG CANDIDATES FOR THE TREATMENT OF TRIPLE-NEGATIVE BREAST CANCER

(71) Applicant: KING FAISAL UNIVERSITY, Al-Ahsa (SA)

(72) Inventors: Saad Shaaban, Al-Ahsa (SA); Hany Mohamed Abd El-Lateef Ahmed, Al-Ahsa (SA); Bander Alshemary, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/386,231

(22) Filed: Nov. 1, 2023

Related U.S. Application Data

(62) Division of application No. 18/217,084, filed on Jun. 30, 2023.

(51) Int. Cl.
| | |
|---|---|
| *C07D 487/14* | (2006.01) |
| *A61K 31/506* | (2006.01) |
| *C07D 239/74* | (2006.01) |
| *C07D 471/04* | (2006.01) |
| *C07D 471/14* | (2006.01) |

(52) U.S. Cl.
CPC ......... *C07D 239/74* (2013.01); *C07D 471/04* (2013.01); *C07D 471/14* (2013.01)

(58) Field of Classification Search
CPC .. C07D 487/14; C07D 487/04; A61K 31/506; A61P 35/00; A61P 25/28
USPC ........................ 544/251, 281; 514/257, 259.1
See application file for complete search history.

(56) References Cited

U.S. PATENT DOCUMENTS

| 11,845,750 B1 * | 12/2023 | Negm ................. C12N 9/0028 |
| 2017/0175197 A1 | 6/2017 | Gatalica et al. |
| 2018/0045727 A1 | 2/2018 | Spetzler et al. |
| 2023/0116253 A1 | 4/2023 | Codelli et al. |

OTHER PUBLICATIONS

PubChem CID 102084855 (2015).
PubChem CID 122370797 (2016).
PubChem CID 145964997 (2020).
Singh et al., "Role of PARP in TNBC: Mechanism of Inhibition, Clinical Applications, and Resistance", Biomedicines. Nov. 2021; 9(11): 1512.
Liao et al., "Targeting regulated cell death (RCD) with small-molecule compounds in triple-negative breast cancer: a revisited perspective from molecular mechanisms to targeted therapies", Journal of Hematology & Oncology vol. 15, Article No. 44 (2022).
Jhan et al., "Triple-negative breast cancer and the potential for targeted therapy", Pharmacogenomicsvol. 18, No. 17 (2017).

* cited by examiner

*Primary Examiner* — Charanjit Aulakh
(74) *Attorney, Agent, or Firm* — Nath, Goldberg & Meyer; Richard C. Litman

(57) ABSTRACT

Multitarget-directed compounds combining the features of reactive oxygen species (ROS) modulators, poly (ADP-ribose) polymerase 1 (PARP1), and/or heat shock protein 90 (Hsp90) inhibitors in a single molecule. These single agents constitute a systemic regimen for treating the triple-negative breast cancer phenotype that overcomes drug resistance and tumor recurrence, and may be used for other indications as well, such as the treatment of various neurodegenerative disorders.

7 Claims, 1 Drawing Sheet

MULTI-TARGET DRUG CANDIDATES FOR THE TREATMENT OF TRIPLE-NEGATIVE BREAST CANCER

CROSS-REFERENCE TO RELATED APPLICATION

This application is a divisional of U.S. patent application Ser. No. 18/217,084, filed on Jun. 30, 2023, the entire contents of which are incorporated herein by reference.

BACKGROUND

1. Field

The disclosure of the present patent application relates to novel multifunctional compounds combining the features of ROS modulators, PARP1, and/or Hsp90 inhibitors in a single molecule, in particular the use of such compounds for treating triple-negative breast cancer.

2. Description of the Related Art

Triple-negative breast cancer (TNBC) accounts for 20-25% of all breast cancers and is characterized by its aggressive clinical behavior, poor prognosis, and high recurrence rates. TNBC lacks the overexpression of the estrogen receptor (ER), the progesterone receptor (PR), and the human epidermal growth factor 2 receptor (HER2), and therefore, cytotoxic chemotherapy remains the only therapeutic option. Although chemotherapy has shown to be effective in early-stage TNBC disease, patients in advanced disease states respond poorly to these drugs. Furthermore, drug resistance and a high risk of relapse were constantly observed in early and advanced stages. These are attributed to the complicated and multifaceted nature of TNBC, which results from combined biochemical alterations, sequential mutations, and modification in gene expression occurring at various genetic levels and pathways. To target this multifactorial mechanistic nature of TNBC, novel multitarget drug candidates are needed to interact with these multiple altered events and pathways.

Among the various TNBC alterations, BRCA1 dysregulation and increased generation of reactive oxygen species (ROS) have recently emerged as potential therapeutic targets. Further, recent genomic, biological, and molecular investigations have shown that intrinsic TNBC heterogeneity is the result of a combination of both genetic and biochemical alterations. These include low levels of hormone receptor-related genes (ER and PR), absence of HER2, BRCA1 dysregulation, and overexpression of specific proteins (e.g., Hsp90, EGFR, VEGF, p53, p15, and cyclin E in addition to glycolysis- and mitochondrial metabolism-related proteins). These are ultimately associated with metabolic phenotype and mitochondrial dysfunction in addition to a disturbance in the intracellular redox network. The latter encompasses high levels of ROS, reactive nitrogen species (RNS), and metal ions as well as reduced antioxidant capacity. Therefore, the development of more effective TNBC therapies with high clinical impact requires an extensive understanding of the above sophisticated biochemical and genetic abnormalities.

Heat shock protein 90 (Hsp90) inhibition has the potential to simultaneously stop the function of proteins associated with high expression TNBC recurrence and chemotherapy resistance and subsequently suppress tumor growth. In addition, Hsp90 inhibitors can overcome drug resistance due to secondary mutations of a target protein. On the other hand, increased generation of ROS and oxidative stress (OS) were also common features in TNBC. In this regard, ROS modulation can be exploited therapeutically for the preferential elimination of cancer cells. Although these targeted strategies have individually shown enhanced preclinical treatment response, none of them were approved by the US Food and Drug Administration (FDA). Moreover, no apparent, proven, and effective single agent has been demonstrated to provide a systemic regimen recommended for treating the triple-negative phenotype that overcomes drug resistance and tumor recurrence. Given the high morbidity and mortality of TNBC, the lack of available specific drugs necessitates developing more targeted and less toxic therapies to overcome drug resistance and expand the available effective drug arsenal to battle this disease.

Thus, new multitarget drug candidates solving the aforementioned problems are desired.

SUMMARY

The present subject matter relates to novel multifunctional compounds that can simultaneously interfere with multiple altered pathways, making them effective, for example, in the treatment of triple-negative breast cancer (TNBC). Consequently, the present subject matter relates to multitarget-directed compounds combining the features of reactive oxygen species (ROS) modulators, poly (ADP-ribose) polymerase 1 (PARP1), and/or heat shock protein 90 (Hsp90) inhibitors in a single molecule. Accordingly, for the first time, the present subject matter relates to an effective single agent constituting a systemic regimen for treating the triple-negative breast cancer phenotype that overcomes drug resistance and tumor recurrence.

In an embodiment, the present subject matter relates to a multi-functional agent having the formula I:

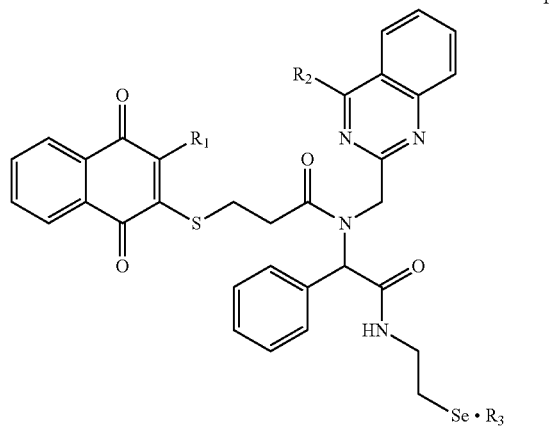

wherein: $R_1$ is a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group; $R_2$ is H, a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group; and $R_3$ is a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group.

In another embodiment, the present subject matter relates to a method of making the multi-functional agent of formula I, the method comprising: reacting, at room temperature, a quinazolin-2-ylmethanamine with benzaldehyde in methanol, then adding a 3-((1,4-dioxo-1,4-dihydronaphthalen-2-yl)thio)propanoic acid and a 2-isocyanoethylselane to obtain the multifunctional agent according to the following reaction scheme:

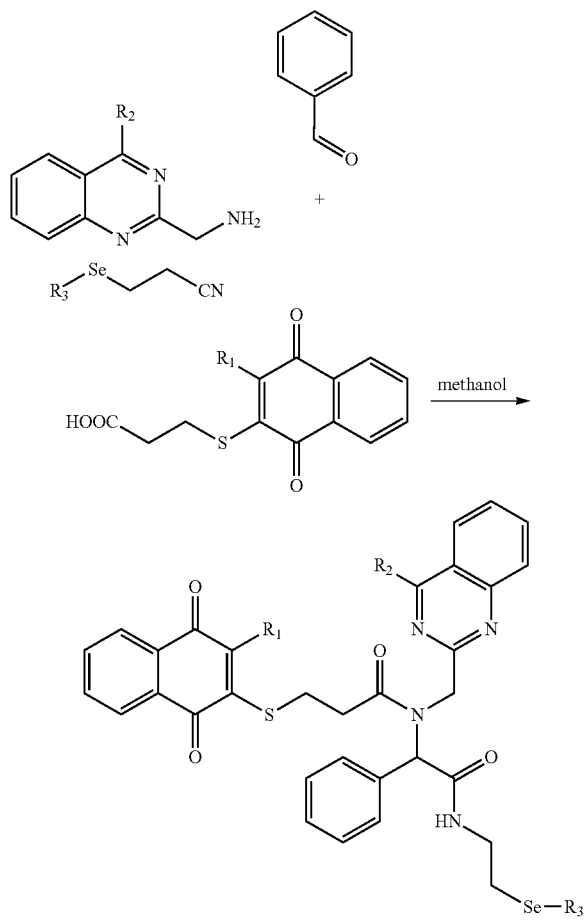

wherein: $R_1$ is a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group; $R_2$ is H, a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group; and $R_3$ is a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group.

In another embodiment, the present subject matter relates to a multi-functional agent having the formula II:

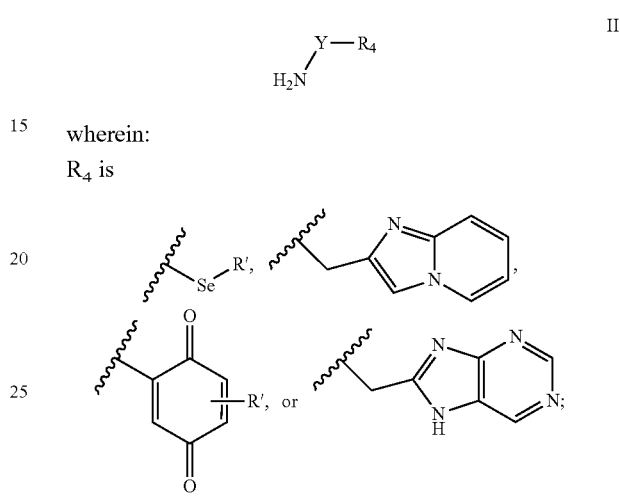

wherein:

$R_4$ is

R' is H, a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group; and Y is guanine, cytosine, or adenine.

In a further embodiment, the present subject matter relates to a method of making the multi-functional agent of formula II, the method comprising: reacting 2-(phenylselanyl)acetaldehyde and tert-butyl isocyanide with guanidine, cytosine, or adenine in DMSO according to the following reaction scheme:

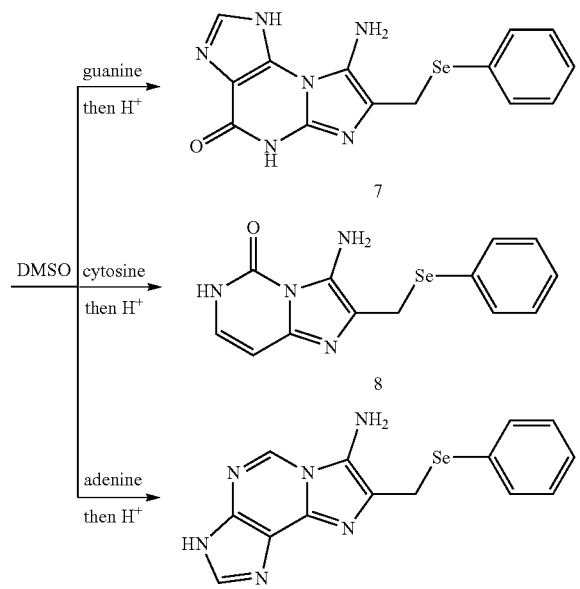

In an embodiment, the present subject matter relates to a pharmaceutical composition, comprising a multi-functional agent as described herein and a pharmaceutically acceptable carrier.

In a further embodiment, the present subject matter relates to a method of treating cancer in a patient, the method comprising: administering a multi-functional agent as described herein to a patient in need thereof. Similarly, the present subject matter also relates to a method of treating a neurodegenerative disorder in a patient, the method comprising: administering a multi-functional agent as described herein to a patient in need thereof.

These and other features of the present subject matter will become readily apparent upon further review of the following specification.

DETAILED DESCRIPTION OF THE PREFERRED EMBODIMENTS

Figure 1:
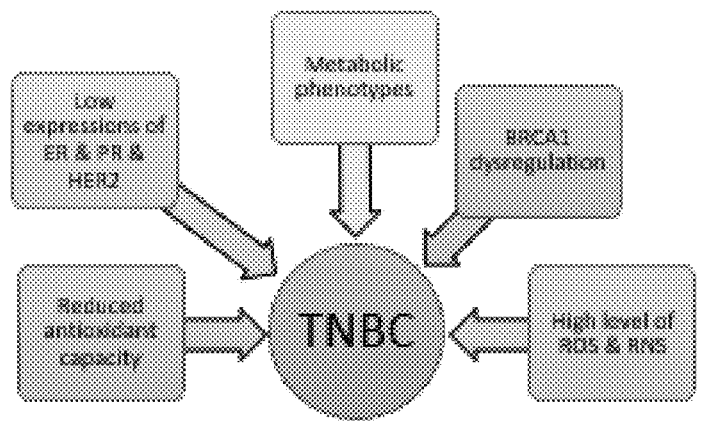
FIG. 1 depicts a chart showing how TNBC cells are characterized by increased production of ROS, decreased antioxidants, low expression of hormone receptor (ER and PR) and HER-2-related genes, metabolic abnormalities and BRCA1 mutations.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. In other embodiments, alkyl groups can be optionally substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group) or 2 to 6 carbon atoms (i.e., $C_2$-$C_6$ alkenyl group). In some embodiments, alkenyl groups can be substituted as described herein. In other embodiments, alkenyl groups can be optionally substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "substituted alkenyl" as used herein refers to an alkenyl group in which 1 or more (up to about 5, for example about 3) hydrogen atoms is replaced by a substituent independently selected from those listed above with respect to a substituted alkyl. Other alkenyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl". In certain embodiments, an aryl group is substituted with another aryl group and can be referred to as a biaryl group. Each of the aryl groups in the biaryl group can be substituted, or optionally substituted, as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted, or optionally substituted, as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers. Unless defined otherwise, all technical and scientific terms used herein have the same meaning as commonly understood to one of ordinary skill in the art to which the presently described subject matter pertains. Accordingly, "isomers" or "stereoisomers" of all compounds described herein are contemplated as falling within the scope of the presently disclosed subject matter.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

As described herein, "room temperature" means a temperature of about 25° C.

The present subject matter relates to novel multifunctional compounds that can simultaneously interfere with multiple altered pathways, making them effective, for example, in the treatment of triple-negative breast cancer (TNBC). Consequently, the present subject matter relates to multitarget-directed compounds combining the features of reactive oxygen species (ROS) modulators, poly (ADP-ribose) polymerase 1 (PARP1), and/or heat shock protein 90 (Hsp90) inhibitors in a single molecule. Accordingly, for the first time, the present subject matter relates to an effective single agent constituting a systemic regimen for treating the triple-negative breast cancer phenotype that overcomes drug resistance and tumor recurrence.

Although PARP1 and Hsp90 inhibitors seem to have different therapeutic targets than ROS modulators, both run on the same track. Increased ROS generation by ROS modulators leads to DNA double-strand breaks, which is quite similar to the molecular mode of action displayed by PARP1 inhibitors. At the same time, these ROS modulators have the potential to cleave and deactivate Hsp90. The value of synthetic libraries relies on their feasibility (easy access) and their probability to hit the biological target(s), which is related to their diversity and complexity.

It has been a major challenge to install not just one or two but three or more distinct pharmacophores in one single molecule. A one-pot single-step synthetic strategy using stable reagents under neutral conditions is therefore employed herein, i.e., the isocyanide-based multicomponent (IMCR) Ugi and Groebke-Blackburn-Bienaymé (GBB) reactions, as described in more detail below.

In an embodiment, the present subject matter relates to a multi-functional agent having the formula I:

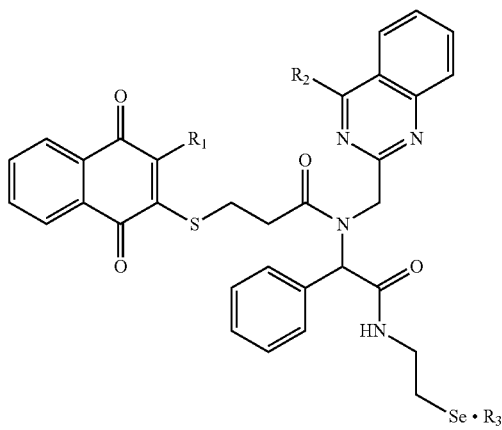

wherein: $R_1$ is a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group; $R_2$ is H, a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group; and $R_3$ is a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group.

In an embodiment, the present subject matter relates to a multi-functional agent of formula I, wherein: $R_1$ is a $C_1$-$C_6$ alkyl group; $R_2$ is H; and $R_3$ is an aryl group.

In another embodiment, the present subject matter relates to a multi-functional agent of formula I, having the formula:

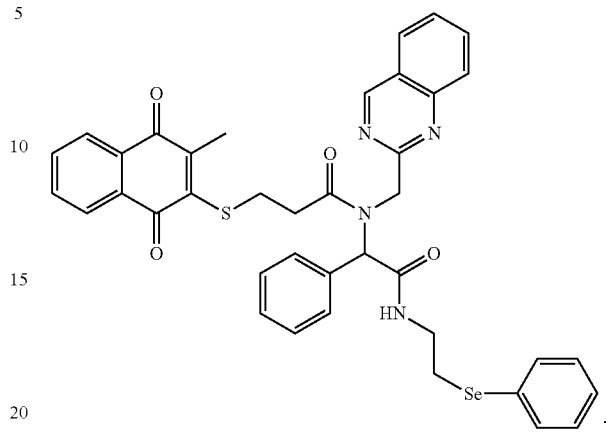

In an embodiment, the present subject matter relates to a multi-functional agent having the formula II:

wherein:
$R_4$ is

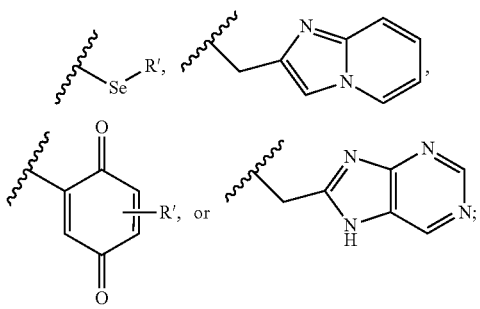

R' is H, a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group; and Y is guanine, cytosine, or adenine.

In a further embodiment, the present subject matter relates to a multi-functional agent of formula II, wherein $R_4$ is

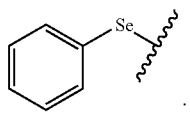

In still another embodiment, the present subject matter relates to a multi-functional agent of formula II, selected from the group consisting of:

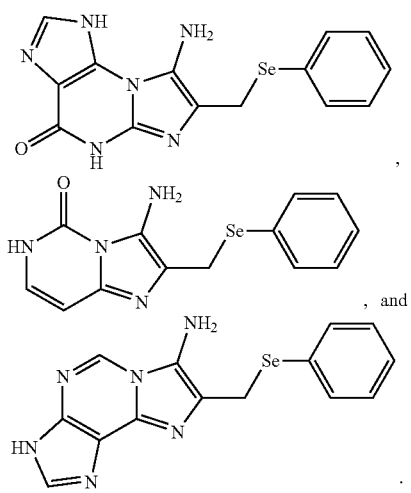

,

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formulae I and II and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or the salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formulae I and II, as well as the solvates of the salts, the stereoisomers and the salts of the stereoisomers of the compounds of formulae I and II.

In obtaining the present compounds in their solvate form, the present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formulae I and II and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present subject matter relates to the use of a one-pot single-step synthetic method, i.e., the isocyanide-based multicomponent (IMCR) Ugi and Groebke-Blackburn-Bienaymé (GBB) reactions, to prepare the present multi-functional agents. These reactions are promising synthetic tools in the context of Diversity Oriented Synthesis and are used to achieve high levels of efficiency, complexity, and diversity in a single step (short reaction sequences: brevity) by varying each component participating in the reaction. Combining simple and flexible building blocks gives rise to the present novel complex structures by the simultaneous formation of two or more bonds.

Moreover, the present synthetic methods are notable for their ease of automation, simplicity, superior atom economy, ability to obtain a large number of compounds with minimal effort, reduced reaction time and cost, and formation of pure products with avoidance of tedious workup and purification.

By using readily available quinone, selenium, quinazoline, and/or purines and/or imidazopyridines building blocks in Ugi reactions, diverse libraries of structurally rather complex ROS modulators can be synthesized. One additional advantage of these specific types of I-MCRs, the product nature, i.e., typically carboxamides (α-acylamino carboxamides), are obtained which are common structures in many PARP1 inhibitors. So, in this case, these I-MCRs would deliver libraries of ROS modulators/Hsp90 with expected PARP1 inhibitor activity.

For example, diverse libraries of structurally rather complex PARP1 inhibitors and ROS modulators can be synthesized using the readily available selenoquinone (1) and amino quinazoline (2) in the Ugi reaction. So, in this case, this strategy would deliver libraries of ROS modulators and PARP1 inhibitor activity.

Accordingly, in an embodiment, the present subject matter relates to a method of making the multi-functional agent of formula I, the method comprising: reacting, at room temperature, a quinazolin-2-ylmethanamine with benzaldehyde in methanol, then adding a 3-((1,4-dioxo-1,4-dihydronaphthalen-2-yl)thio)propanoic acid and a 2-isocyanoethylselane to obtain the multifunctional agent according to the following reaction scheme:

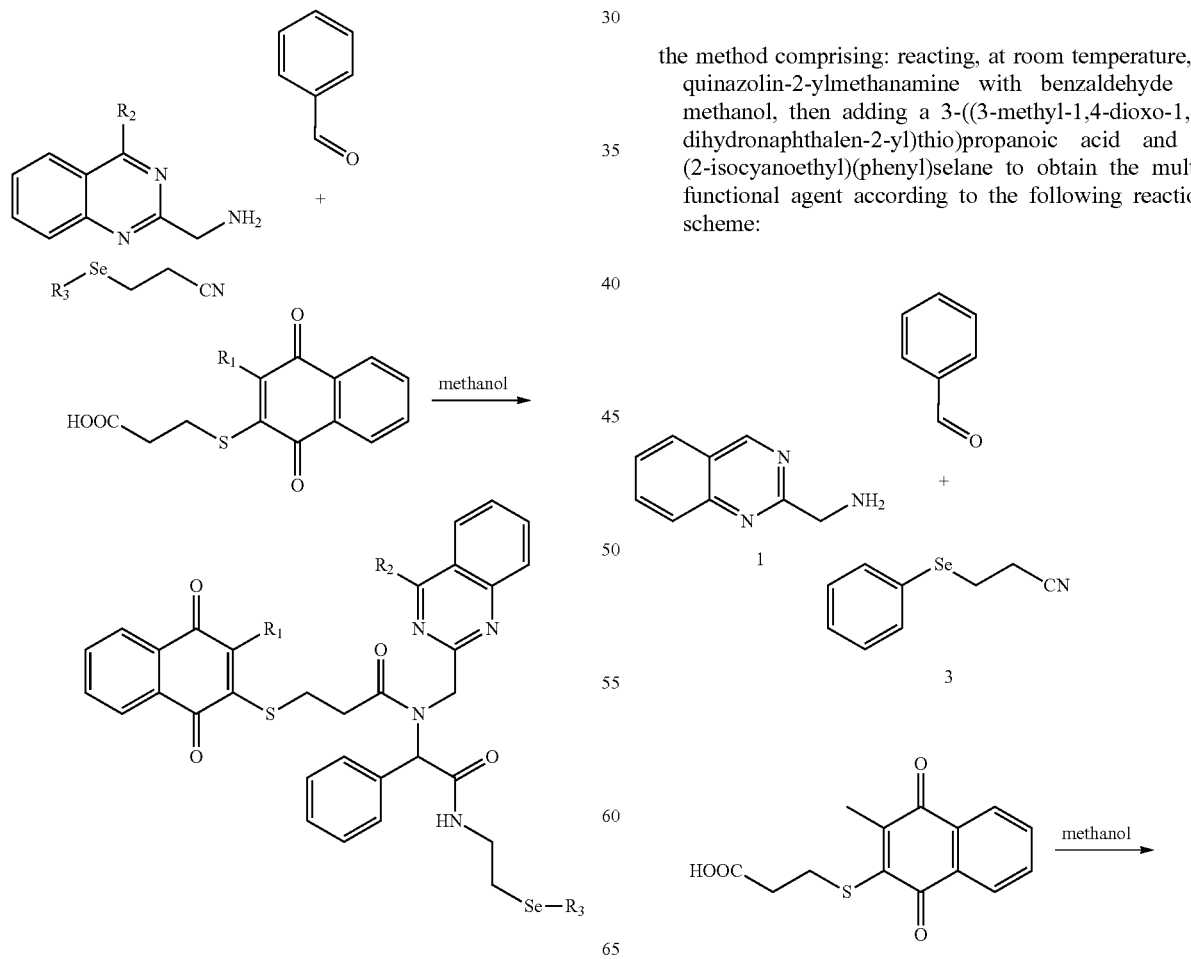

wherein: $R_1$ is a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group; $R_2$ is H, a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group; and $R_3$ is a $C_1$-$C_6$ alkyl group, a $C_2$-$C_6$ alkenyl group, an aryl group, a heteroaryl group, a $C_3$-$C_8$ cycloalkyl group, or a $C_3$-$C_8$ cycloalkenyl group.

In another embodiment, the present subject matter relates to a method of making a multi-functional agent having the formula:

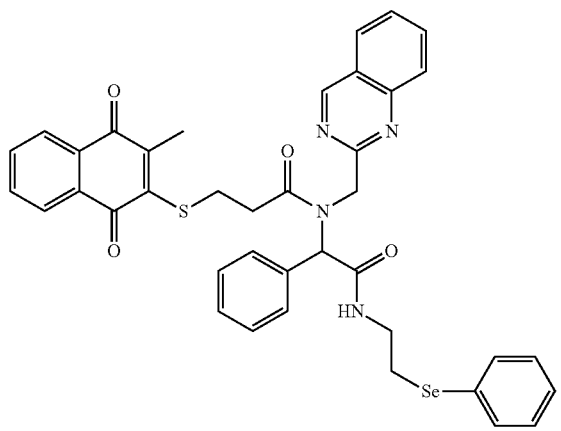

the method comprising: reacting, at room temperature, a quinazolin-2-ylmethanamine with benzaldehyde in methanol, then adding a 3-((3-methyl-1,4-dioxo-1,4-dihydronaphthalen-2-yl)thio)propanoic acid and a (2-isocyanoethyl)(phenyl)selane to obtain the multifunctional agent according to the following reaction scheme:

-continued

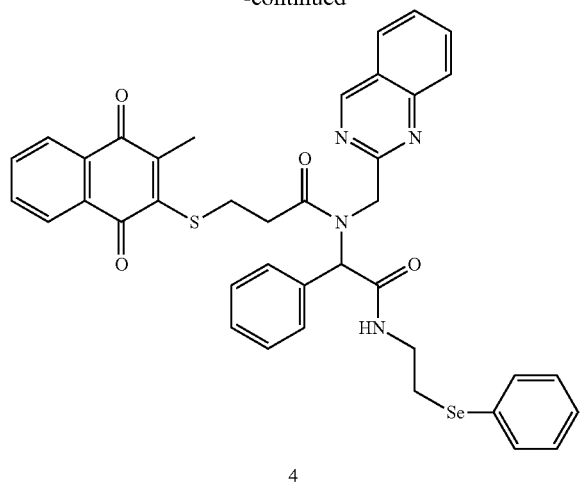

4

In certain embodiments in this regard, the quinazolin-2-ylmethanamine, benzaldehyde, 3-((3-methyl-1,4-dioxo-1,4-dihydronaphthalen-2-yl)thio)propanoic acid, and (2-isocyanoethyl)(phenyl)selane can be reacted in an about 1:1.1:1.1:1.1 molar ratio.

In a further embodiment, the present subject matter relates to a method of making the multi-functional agent of formula II, the method comprising: reacting 2-(phenylselanyl)acetaldehyde and tert-butyl isocyanide with guanidine, cytosine, or adenine in DMSO according to the following reaction scheme:

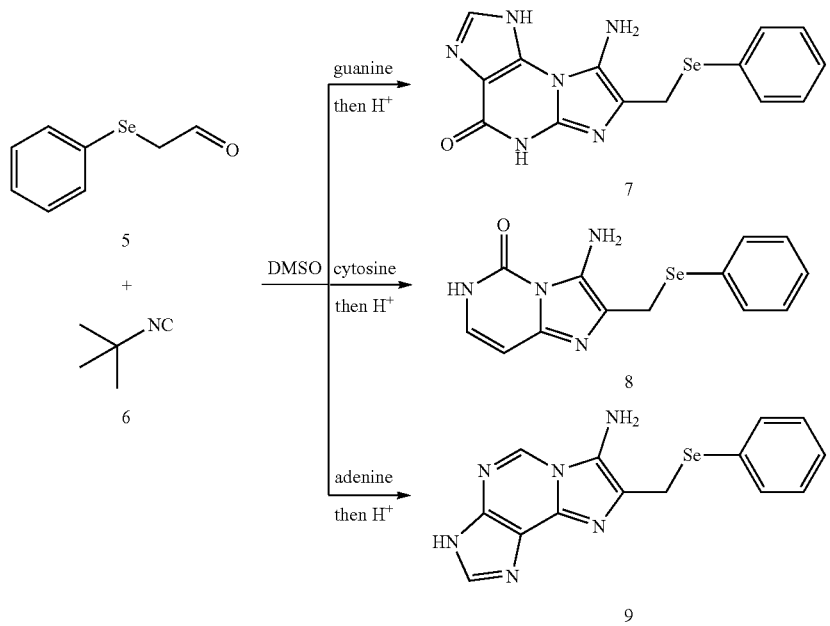

In this regard, in the method for making compound 9 shown above, the reaction can occur in DMSO under nitrogen at a temperature of about 65° C. to about 75° C., about 65° C., about 66° C., about 67° C., about 68° C., about 69° C., about 70° C., about 71° C., about 72° C., about 73° C., about 74° C., about 75° C., or about 70° C., for at least about 8 hour.

In certain embodiments in this regard, the tert-butyl isocyanide and guanidine, cytosine, or adenine are reacted in an about 1:1.1 molar ratio.

In an embodiment, the present subject matter relates to a pharmaceutical composition, comprising a therapeutically effective amount of a multi-functional agent as described herein and a pharmaceutically acceptable carrier. In this regard, the pharmaceutically acceptable carrier can be one or more pharmaceutically acceptable carriers, excipients, or vehicles. In some embodiments, the present compositions can be used for combination therapy, where other therapeutic and/or prophylactic ingredients can be included therein.

In an embodiment, the pharmaceutical composition comprises one or two of the present multi-functional agents, or one of the present multi-functional agents.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 23rd Edition. Easton, Pa., Mack Publishing Company, 2020, the entire contents of which are incorporated by reference herein.

The present multi-functional agents are typically administered at a therapeutically or pharmaceutically effective dosage, e.g., a dosage sufficient to provide treatment for, e.g., a cancer or a neurodegenerative disorder. Administration of the multi-functional agents or pharmaceutical compositions thereof can be by any method that delivers the multi-functional agents systemically and/or locally. These methods include oral routes, parenteral routes, intraduodenal routes, and the like.

While human dosage levels have yet to be optimized for the present multi-functional agents, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present multi-functional agents for treatment of a disease, disorder, or condition, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present multi-functional agents can also be administered in sustained or controlled release dosage forms, including depot injections, osmotic pumps, pills, transdermal (including electrotransport) patches, and the like, for the prolonged administration of the multi-functional agents at a predetermined rate, preferably in unit dosage forms suitable for single administration of precise dosages.

The present multi-functional agents may also be administered as compositions prepared as foods for foods or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present multi-functional agents, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active multi-functional agent as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active multi-functional agent in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active multi-functional agent contained in such parenteral compositions is highly dependent on the specific nature thereof, as well as the activity of the multi-functional agent and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active multi-functional agent alone or in combination with other pharmaceutically acceptable excipients can also be administered.

Formulations of the active multi-functional agent may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

In a further embodiment, the present subject matter relates to a method of treating cancer in a patient, the method comprising: administering a multi-functional agent as described herein to a patient in need thereof. In certain embodiments, the cancer can be triple-negative breast cancer (TNBC).

In this regard, TNBC has been a particularly difficult disease, and form of breast cancer, to treat as TNBC cells are characterized by increased production of ROS, decreased antioxidants, low expression of hormone receptor (ER and PR) and HER-2-related genes, metabolic abnormalities and BRCA1 mutations, as shown in FIG. 1. Accordingly, the present multi-functional agents are uniquely suited to treat TNBC, as these agents combine the features of ROS modulators, poly (ADP-ribose) polymerase 1 (PARP1), and/or heat shock protein 90 (Hsp90) inhibitors in a single molecule. In particular, TNBC should be particularly susceptible to a multitarget drug strategy as a basis for therapeutic selectivity involving cell death-associated mechanisms of combinatorial ROS modulators and PARP1 and Hsp90 inhibitors. Such methods of treatment were previously only available by the combined use of multiple active agents, whereas the present multi-functional agents for the first time provide treatment involving all these pathways by administration of a single active agent.

Figure 2:
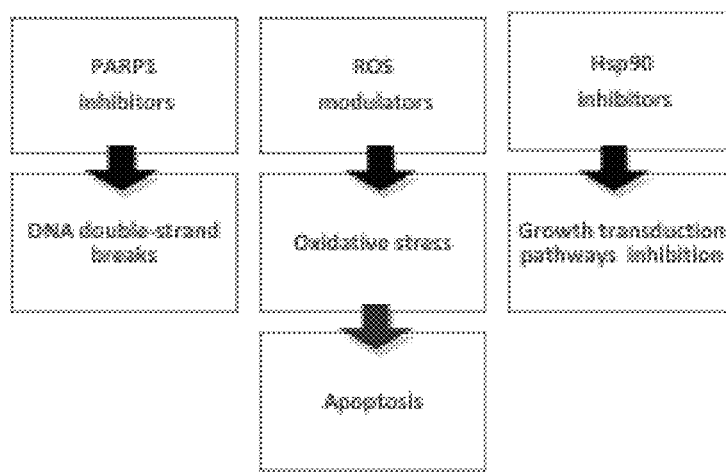
FIG. 2 depicts a chart showing a multitarget-directed drug strategy as a basis for therapeutic selectivity.

Although individual PARP1 and Hsp90 inhibitors have different therapeutic targets than ROS modulators, the combination strategy employed herein can have a synergetic effect. Increased ROS generation by ROS modulators leads to DNA double-strand breaks, similar to the molecular mode of action displayed by PARP1 inhibitors. However, at the same time, these ROS have the potential to cleave and deactivate Hsp90, as shown in FIG. 2.

This strategy has several advantages over conventional methods. By way of non-limiting example, the present multi-functional agents are designed to be compatible with the harsh TNBC microenvironment conditions (e.g., OS, genetic alterations). Further, the use of the present multi-functional agents allows targets to be carefully chosen to selectively induce cancer cell death with minimal toxic effect to normal cells. In addition, blocking Hsp90 can lead to reduction of drug resistance and metastasis because the mutated/upregulated oncogenic proteins are usually Hsp90 clients. Likewise, combining two or more pharmacophores with a different therapeutic target(s) in one single molecule, as has been achieved by the present multi-functional agents, can synergistically potentiate their corresponding chemotherapeutic cytotoxicity, thereby allowing them to be introduced at much lower concentrations than usual. Finally, this strategy is not limited to TNBC, but it can also be applied to other cancer cells or diseases comprising similar clinical behavior (e.g., neurodegenerative disorders).

Accordingly, the present subject matter also relates to a method of treating a neurodegenerative disorder in a patient, the method comprising: administering a multi-functional agent as described herein to a patient in need thereof. In certain embodiments, the neurodegenerative disorder can be one or more of Parkinson's Disease, Alzheimer's Disease, Huntington's Disease, Amyotrophic Lateral Sclerosis (ALS), and motor neuron disease. In addition, administration of the present multi-functional agents to a patient can treat both the cancer and the neurodegenerative disorder simultaneously.

The present teachings are illustrated by the following examples.

EXAMPLES

Example 1

PARP1 Inhibitors and ROS Modulators

The synthesis of ROS modulators can include quinones and organoselenium scaffolds as described in Scheme 1. Additionally, two classes of PARP1 inhibitors can be integrated in the synthesis strategy. These involve carboxamide and quinazoline pharmacophores. These compounds can exhibit structural similarities to the natural PARP-1 enzyme substrate, nicotinamide adenine dinucleotide (NAD$^+$), and thus exert their inhibitor activity by occupying the nicotinamide pocket.

Scheme 1

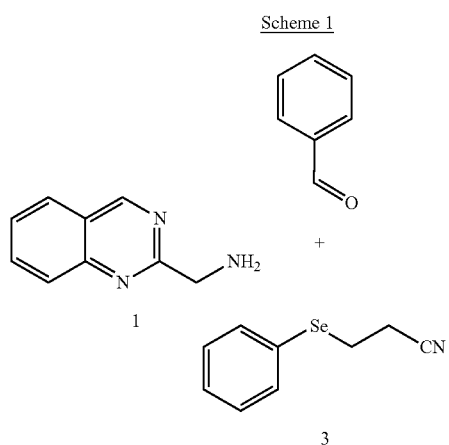

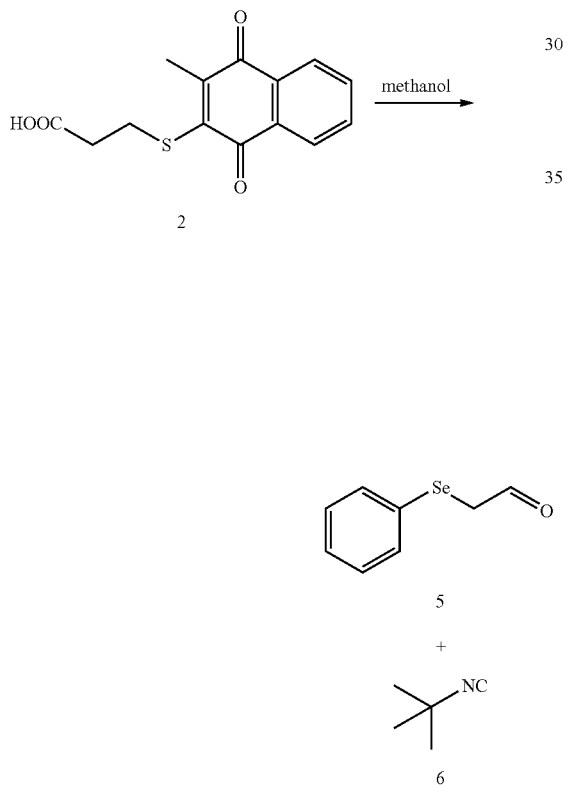

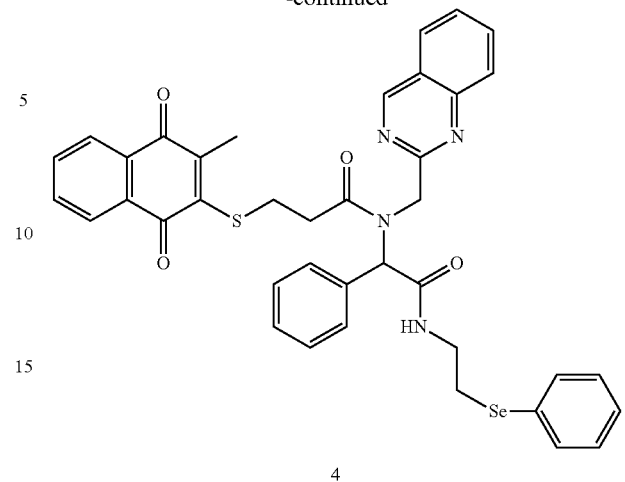

The target compound 4 was synthesized according to the Ugi isocyanide-based multicomponent strategy. The reaction started with the reaction of quinazolin-2-ylmethanamine (1) (1 mmol) with benzaldehyde (1.1 mmol) in methanol (1 ml), followed by the addition of 3-((3-methyl-1,4-dioxo-1,4-dihydronaphthalen-2-yl)thio)propanoic acid (2) (1.1 mmol) and (2-isocyanoethyl)(phenyl)selane (3) (1.1 mmol) at room temperature.

Example 2

Hsp90 Inhibitors and ROS Modulators

Synthetic purines and imidazopyridines are used as small molecule Hsp90 inhibitors as they mimic the purine base of the ADP/ATP and competitively bind to Hsp90, thereby blocking ATP binding to Hsp90 and inhibiting Hsp90 function. Therefore, GBBR was used for the synthesis of aminoimidazole-condensed nucleobases (Hsp90 inhibitors) by the inclusion of the 2-amidine functionality of adenine, guanine or cytosine as shown in Scheme 2.

Scheme 2

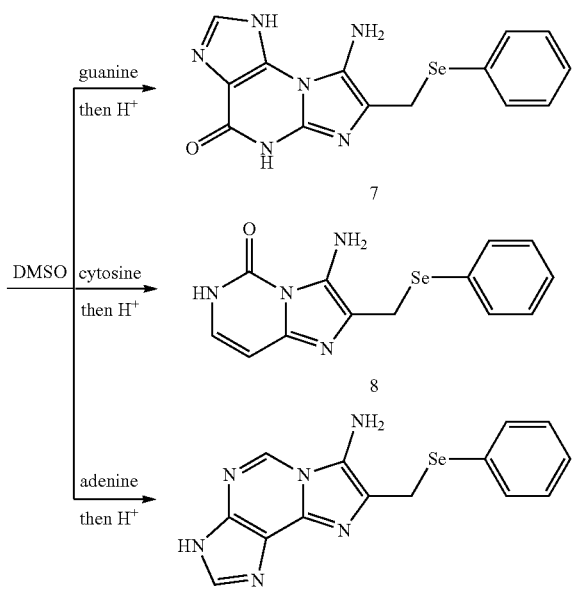

Scheme 2 represents the synthesis of purines and imidazopyridines which in turn are Hsp90 inhibitors as they mimic the purine base of the ADP/ATP and competitively bind to Hsp90, thereby blocking ATP binding to Hsp90 and inhibiting Hsp90 function.

The target compounds 7, 8, and 9 were synthesized according to the GBB isocyanide-based multicomponent strategy. The reaction started by the reaction of 2-(phenylselanyl)acetaldehyde (5), tert-butyl isocyanide (6) (1 mmol) with either guanine, cytosine, or adenine (1.1 mmol) in DMSO (1 ml) under nitrogen and at 70° C. for 8 hrs.

It is to be understood that the multi-functional agents are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A multi-functional agent having the formula II:

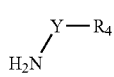

wherein:

R$_4$ is

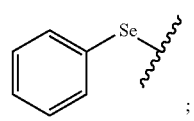 [SMILES: *[Se]c1ccccc1]

and

Y is guanine, cytosine, or adenine.

2. The multi-functional agent of claim 1, selected from the group consisting of:

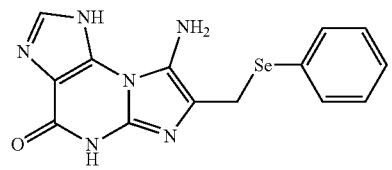

,

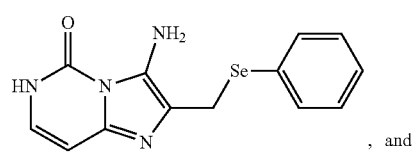

, and

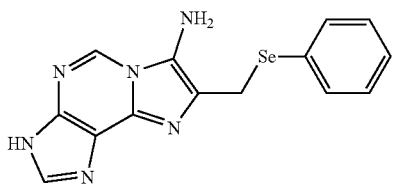

.

3. A method of making the multi-functional agent of claim 2, the method comprising:

reacting 2-(phenylselanyl)acetaldehyde and tert-butyl isocyanide with guanidine, cytosine, or adenine in DMSO according to the following reaction scheme:

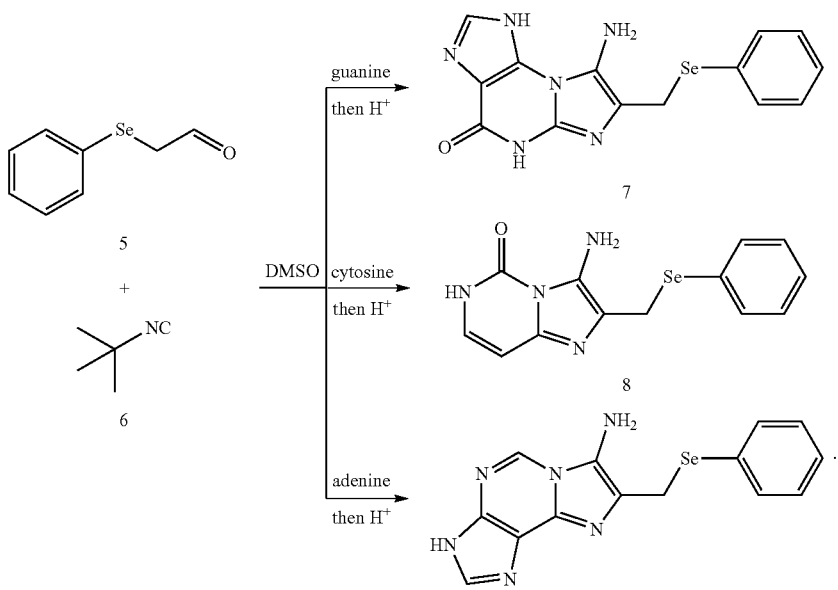

4. The method of claim 3, wherein the reaction occurs in DMSO under nitrogen at a temperature of about 65° C. to about 75° C. for at least about 8 hours.

5. The method of claim 3, wherein the tert-butyl isocyanide, and guanidine, cytosine, or adenine are reacted in an about 1:1.1 molar ratio.

6. A pharmaceutical composition, comprising a therapeutically effective amount of the multi-functional agent of claim 1 and a pharmaceutically acceptable carrier.

7. A method of treating cancer in a patient, the method comprising:
   administering the multi-functional agent of claim 1 to a patient in need thereof;
   wherein the cancer is triple-negative breast cancer.

* * * * *